United States Patent
Ahn et al.

(10) Patent No.: US 7,179,479 B1
(45) Date of Patent: Feb. 20, 2007

(54) **MOSQUITO REPELLENT ISOLATED FROM *FOENICULUM VULGARE* FRUIT**

(75) Inventors: Young-Joon Ahn, Seoul (KR); Do-Hyoung Kim, Incheon (KR); Soon-Il Kim, Kyunggi-do (KR)

(73) Assignee: Naturobiotech Co., Ltd., Suwon (KR)

( * ) Notice: Subject to any disclaimer, the term of this patent is extended or adjusted under 35 U.S.C. 154(b) by 134 days.

(21) Appl. No.: 10/332,168

(22) PCT Filed: Oct. 2, 2000

(86) PCT No.: PCT/KR00/01097

§ 371 (c)(1), (2), (4) Date: Jan. 3, 2003

(87) PCT Pub. No.: WO02/02065

PCT Pub. Date: Jan. 10, 2002

(30) Foreign Application Priority Data

Jul. 5, 2000 (KR) .............................. 2000-38336

(51) Int. Cl.
  *A01N 25/32* (2006.01)
(52) U.S. Cl. .................... 424/406; 424/405; 424/750; 424/DIG. 10; 514/560; 514/692; 514/919
(58) Field of Classification Search .............. 424/405, 424/DIG. 10, 725; 514/919, 588, 560
See application file for complete search history.

(56) References Cited

FOREIGN PATENT DOCUMENTS

CH 1059657 A 3/1992
JP 61-260012 11/1986

OTHER PUBLICATIONS

H.S. Shukla et al., Insect repellant property of essential oils of *Foeniculum volgare*, Pimpinella anisum and Anethole, Pesticides, pp. 33-35, Jan. 1989.

Yih-Shen Hwang et al., Structure-Activity Relationship of Unsaturated Fatty Acids as Misquito Ovipositional Repellents, J. Chem. Ecology, vol. 10, No. 1, pp. 145-151, 1984.

Yih-Shen Hwang et al., Evaluation of Unsaturated Fatty Acids as Mosquito Ovipositional Repellents, pp. 87-88.

Uzi Ravid et al., Chiral GC Analysis of Enantiomerically Pure Fenchone in Essential Oils, Flavour and Frangrance Journal, vol. 7, pp. 169-172, 1992.

J. Karlsen et al., Studies on the Fruits of Foeniculum Species and Their Essential Oil, Planta Med Aug. 1969; 17(3): 281-93.

Hwang et al. "Structure-Activity Relationship of Unsaturated Fatty Acids as Mosquito Ovipositional Repellants" Journal of Chemical Ecology, vol. 10, No. 1, 145-151 (1984).

Kitajima et al. "Constituents of Fennel. X. New Chromanone and Phenylethanoid Glycosides, and threo-Epoxyanethole" Chem. Pharm. Bull. 47(10) 1448-1450 (1999).

Kim et al. "Repellent Activity of Constituents Identified in *Foeniculum vulgare* Fruit against *Aedes aegypti* (Diptera: Culicidae)" J. Agric. Food Chem. 50, 6993-6996 (2002).

*Primary Examiner*—Neil S. Levy
(74) *Attorney, Agent, or Firm*—Gifford, Krass, Groh, Sprinkle, Anderson & Citkowski, P.C.

(57) ABSTRACT

The present invention relates to an insect repellent isolated from *Foeniculum vulgare* fruit, and more particularly, to an insect repellent comprising one or more compounds selected from the group consisting of fennel oil which is isolated from *Foeniculum vulgare* fruit, (+)-fenchone and E-9-octadecenoic acid. The fennel oil, (+)-fenchone and E-9-octadecenoic acid of the present invention are provided as insect repellent components due to their lack of toxicity to people.

5 Claims, 1 Drawing Sheet

MOSQUITO REPELLENT ISOLATED FROM *FOENICULUM VULGARE* FRUIT

BACKGROUND OF THE INVENTION (a) Field of the Invention

The present invention relates to an insect repellent isolated from *Foeniculum vulgare* fruit, and more particularly, to an insect repellent comprising one or more compounds selected from the group consisting of fennel oil which is isolated from *Foeniculum vulgare* fruit, (+)-fenchone and E-9-octadecenoic acid.

(b) Description of the Related Art

There are about 3000 different species of mosquitoes throughout the world and among said mosquitoes, about 500 species of *Aedes*, about 300 species of *Culex*, and about 350 species of *Anpheles* cause hygienic human suffering (Harwood, R. F. and M. T. James. 1979. Entomology in Human and Animal Health. Macmillan). In Korea, about 51 species of mosquitoes are reported with 20 species of *Aedes*, 18 species of *Culex*, and 7 species of *Anpheles* (Hyo Suk You, 1994. Chack List of Insecta from Korea. Kon-Kuk University Press).

Mosquitoes not only bite humans and animals, but also transmit mosquito-borne diseases such as malaria, encephalitis, yellow fever, and dengue and subsequently cause a lot of human death. Currently, two-thirds of the world's population is exposed to mosquito-borne diseases.

Also, mosquitoes are harmful insects which cause great suffering directly or indirectly through stress caused by bites, such as sleeping interference and restriction of field work (Kettle, D. S. 1991. Medical and Veterinary Entomology. Wiley Interscience Publication. New York).

Among mosquitoes known in Korea, *Anopheles sinensis* cause malaria, Inland brugian filariasis and *Aedes togoi* cause filariasis in the south coast region, *Culex tritaeniorhynchus* cause Japanese encephalitis and *Culex pipiens pallens* and *Culex pipiens molestus* cause trouble with bloodsucking in apartment regions. Thus it is necessary to control these insect pests (Han II Lee. 1998. Medical Entomology (4$^{th}$) Komoonsa, Seoul, 340 pp).

Control of the mosquito population was primarily dependent upon chemical control by application of insecticides. However, use of synthetic organic insecticides has caused harmful side effects such as drug-resistance, toxicity to nontarget organisms, and long-term contamination of the environment (Georghiou, G. P. and Saito, T. 1983. Pest Resistance to Pesticides. Plenum Press, New York and London; National Research Council. 1986. Pesticide Resistance: Strategies and Tactics for Management. National Academy Press, Washington, D.C.; Brown, A. W. A. 1978. Ecology of Pesticides. Academic Press, New York.). Therefore, it is necessary to develop new types of selective alternatives for use as insecticides and methods of controlling insect pests which are non-toxic to humans and the environment while still protecting people from mosquitoes.

Repellents made from natural compounds that inhibit insects' responses are highlighted as new types of insect control agents, and such repellents can prevent insect-borne diseases without harmful side effects such as environmental contamination.

However, because repellents are directly applied to people, they must meet many requirements. Repellents must be nontoxic to humans, long-lasting, nonirritating, inoffensive in odor, chemically stable, effective on the whole body even when applied to only a part of the skin, and so on.

Recently, as the study of plant extracts and plant-derived materials has progressed, secondary metabolites of plants such as terpenoids, phenolics, alkaloids have been issued because they are nontoxic to the body, simple in treatment method, and active against a limited number of species including specific target insects. Therefore, much efforts has been focused on plant materials for potentially useful prodeucts as commercial insecticides or as lead compounds. (Jacobson, M. and Crosby, D. G. 1971. Naturally Occurring Insecticides. Marcel Decker, New York; Elliot, M. 1977. Synthetic pyrethroids, pp. 1–28, in M. Eliott (ed.). Synthetic Pyrethroids. ACS Symp. No. 42, *Amer. Chem. Soc.*, San Francisco, Calif.; Hedin, P. A. 1982. *J. Agric. Food Chem.* 30: 201–215; Arnason, J. T., Philogene, B. J., and Morand, P. 1989. ACS Symp. Ser. No. 387, *Amer. Chem. Soc.*, Washington, D.C., 1989; Isman, M. B. 1995. *Rev. Pestic. Toxicol.* 3:1–20.) The plants containing repelling activity components against mosquitoes have been reported, like as *Lantana camara, Artemisia vulgaris, Eucalyptus* species, and oil from the Neem tree (Dua, V. K., N. C. Gupta, A. C. Pandey and V. P. Sharma. 1996. *J. Am. Mosq. Control Assoc.* 12: 406–408; Sharma, V. P. and M. A. Ansari. 1994. *J. Med. Entomol.* 31: 505–50).

In China, the *Eucalyptus*-derived p-menthan-3,8-diol (PMD) repellent is made from waste distillate after extraction of oil from Lemon Eucalyptus. PMD is less effective than DEET (N,N-diethyl-m-toluamide), but it is effective on *Anopheles* and it is also applied to ticks, flies, and nidges. Also, because PMD does not react with plastic and synthetic fibers as does DEET, it can be applied to such goods and it is very nontoxic (Oral administration test of rat $LD_{50}$ 2,408 mg/kg, epidermal test of rat $LD_{50}$>2,000 mg/kg: Trigg, J. K. 1996. *J. Am. Mosq. Control Assoc.* 12: 243–246).

DEET, the most common mosquito repellent, has been extensively used. In the United States, it is estimated that more than 30% of the population use DEET-containing insect repellent products during the insect-biting seasons and over 30 million packages of DEET products are sold annually (1994). DEET is not only effective on a variety of species of harmful insects such as flies, lice, fleas and ticks, but it is also used on nidges and to protect domestic animals.

On the other hand, Malaria in Korea, which had completely disappeared in the 1970's, has been once again seen since 1993, and 3,330 patients contracted the disease between then and September 1998. As of 1999, the number of Malaria infected patients had not been reduced, but on the contrary, the infection rate of non-official civilians has gradually increased and the malarial region has spread from the neighborhood of the demilitarized zone to the whole northern part of Kyunggido. Recently, the number of cases of Japanese Encephalitis has been reduced, but that is small consolation.

In America, mosquito-borne diseases like Encephalitis and Yellow Fever were rampant in the 1990's, and vector-borne diseases such as West Nile Encephalitis which were not previously known have spread.

Also, due to a rise in temperature and change of the environment due to global warming, the appearance of mosquitoes and subsequent bloodsucking activity is increasing. Thus anxiety about damage by mosquitoes is also increasing.

In this situation, although control of mosquitoes through the known synthetic insecticides and use of repellents that protect from mosquito-borne diseases is increasing, little progress has been made in the development of repellents that can overcome the problems of the currently used repellents.

The typical synthetic repellent DEET has several problems. For example, it has an unpleasant odor, it causes irritation to the skin, and it tends to damage glasses and watch straps as reactions occur with some plastics and rubbers. In addition, due to the most problematic issue, which is rapid and strong penetration of the skin, it is restricted in use. In 1982, it was confirmed that the skin penetration ratio of DEET was 30% after 1 hour under the condition whereby the skin was treated with 300 ug/cm$^2$ DEET, and the ratio was 36% after 12 hours. So, the use of DEET has been restricted on children, hypotensive patients, and people with sensitive skin, and adults also cannot cover more than 30% of the surface area of their body.

Therefore, a novel material is required that can reduce the use of DEET and that includes repelling effects. Although detection of non-toxic substitute plant materials is in progress, the development of repellents meeting the complicated requirements is still lacking.

SUMMARY OF THE INVENTION

It is an object of the present invention to provide an insect repellent, and more particularly a mosquito repellent for replacing the synthetic repellent DEET.

For this object, the present invention provides an insect repellent comprising extracts from *Foeniculum vulgare*.

Also, the present invention provides an insect repellent comprising one or more compounds selected from the group consisting of (+)-fenchone-derived compounds and E-9-octadecenoic acid-derived compounds.

DETAILED DESCRIPTION OF THE INVENTION

Figure 1:
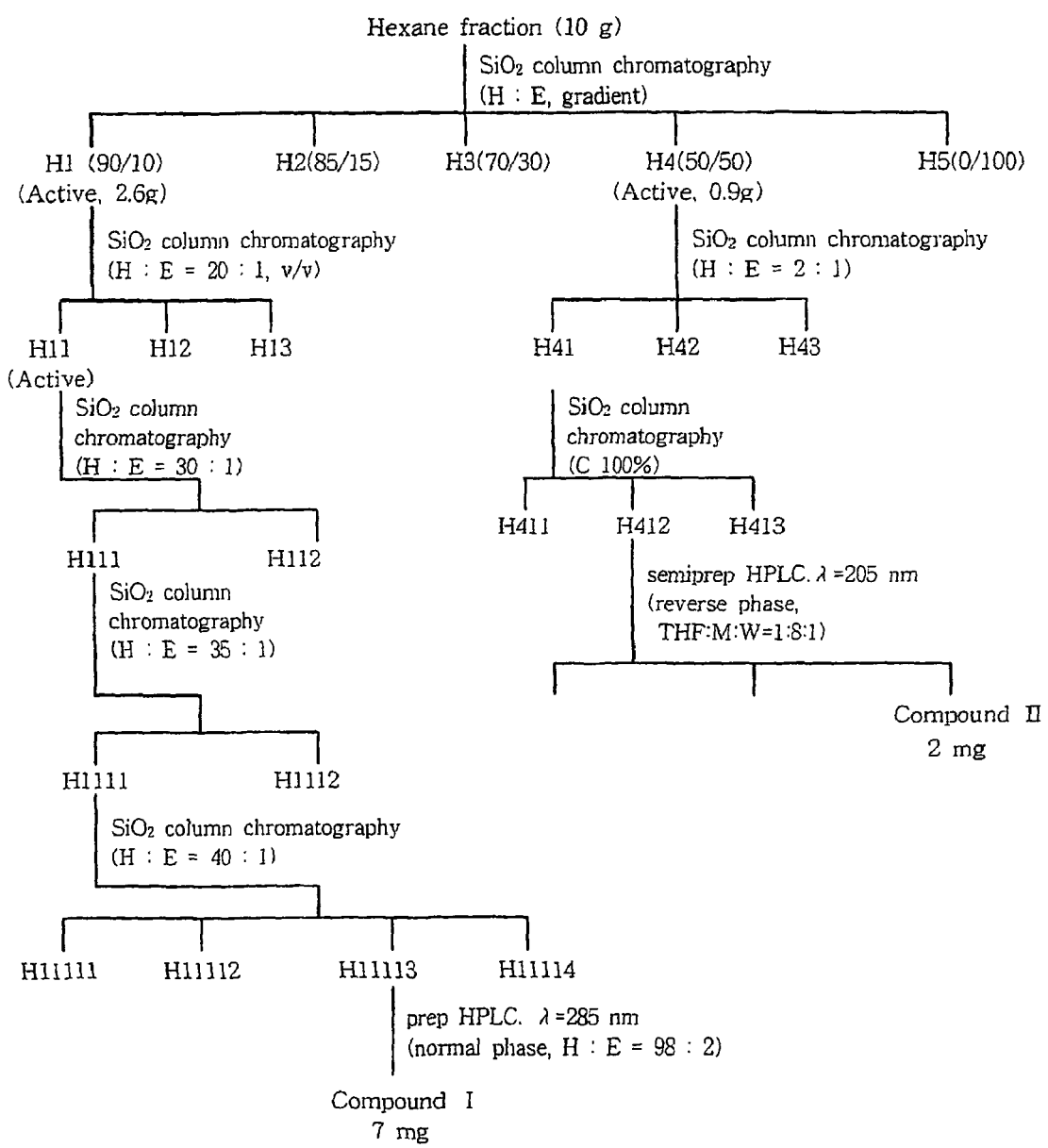
FIG. 1 is a flow chart of the separating steps that isolate the insect repelling compounds from the hexane portion of methanol extracts from *Foeniculum vulgare* fruit.

Fennel or *Foeniculum vulgare* is a perennial or biennial aromatic herb of the family Apiaceae (Umbelliferae). It has a unique flavor and is used as a peptic medicine, for extermination of insects, and as an expectorant in traditional oriental medicine. Also, fennel oil distilled from *Foeniculum vulgare* fruit is used for a liqueur spice and for aromatherapy It is preferred that the repellent of the present invention is used on harmful insects. Harmful insects are those that are directly or indirectly detrimental to humans, for example bloodsucking insects, parasitic insects, pathogenic insects, stinging insects, poisonous insects and generally disagreeable insects. Bloodsucking insects include mosquitoes, gadfly mosquitoes, lice, bedbugs and so on. Parasitic insects include fleas and lice, and pathogenic insects include flies, mosquitoes, croton bugs and lice. Stinging insects include bees, reduviidae species, and poisonous insects include ghungbannalkye, cerambycidae species and Spanish fly. Disagreeable insects include Chironominae, gagiworm and stinkbug. The repellent of the present invention is used on arthropods such as ticks, spiders, centipedes and scorpions, but the preferred harmful insect of this invention is the mosquito.

Also, the usable extracts of the present invention for repelling harmful insects are methanol extracts derived from *Foeniculum vulgare* fruit. The methanol extracts comprise all materials which can be isolated from cells composing *Foeniculum vulgare* fruit. The extraction method and material of said methanol extracts are not completely identical with that of Fennel oil obtained by distillation, but the Fennel oils also include materials from methanol extracts. Accordingly the preferred insect repellent of this invention is fennel oils, and more particularly (+)-fenchone and E-9-octadecenoic acid isolated from methanol extracts from *Foeniculum vulgare* fruit.

The (+)-fenchone and the E-9-octadecenoic acid are materials isolated from *Foeniculum vulgare* and are used for medicinal purposes or as spice. The (+)-fenchone is known as a spice.

The insect repellents of the present invention preferably contain about 65% to 70% of the methanol extracts derived from *Foeniculum vulgare* fruit, and more particularly, about 35% to 40% of fennel oils, 15% to 20% of fenchone or 30% to 35% of E-9-octadecenoic acid. It is also reasonable that the blending ratio of (+)-fenchone and E-9-octadecenoic acid in insect repellents is controlled by using methods applicable to the type of repellents.

The repellent containing *Foeniculum vulgare* fruit of the present invention extract can be formulated as a spray, a solution type ointment and a solid type ointment or gel, and the most preferable repellent is formulated as a solution type ointment.

The experimental method achieved in order to isolate compounds from *Foeniculum vulgare* fruit is outlined below.

In the present invention, the hexane portion, chloroform portion, ethylacetate portion and water-soluble portion were partitioned from the *Foeniculum vulgare* fruit methanol extracts. After the repelling activity of each portion was confirmed by a patch test, the hexane portion having the repelling activity was separated several times by chromatography. In the last separation step, two kinds of repelling compounds were isolated. They were characterized as (+)-fenchone and E-9-octadecenoic acid.

In the present invention, it was proved that methanol extracts and fennel oils isolated from the *Foeniculum vulgare* fruit, (+)-fenchone and E-9-octadecenoic acid repel harmful insects. Through manufacturing an insect repellent comprising fennel oil, (+)-fenchone and E-9-octadecenoic acid, damage by harmful insects may be prevented.

Also, the fennel oils of the present invention were previously proven harmless when commonly employed in medicinal and cosmetic compositions. Thus the (+)-fenchone and the E-9-octadecenoic acid are stable and nontoxic to humans in contrast to the synthetic repellent DEET.

Also, in the present invention, (+)-fenchone and E-9-octadecenoic acid may be used for derivatives in order to develop novel compounds having increased repelling activity and eradication potential against a wide range of insects by modification of the structure of (+)-fenchone and E-9-octadecenoic acid. The derivatives are novel compounds that are obtained by the addition or deletion of OH$^-$ or other chemical structures on the common compounds having special activity, they do not have the problems associated with the known compounds, and they maintain a high activity.

One well-known pyresroide insecticide is a synthetic derivative made from a compound of the essential oil, and it has a lower photolysis effect and higher toxicity than the original material.

Therefore the present invention provides an insect repellent comprising (+)-fenchone derivatives or E-9-octadecenoic acid derivatives.

The present invention will be now explained in more detail by reference to examples which do not limit the present invention.

EXAMPLE 1

Preparation of Sample and Analyzing of Active Compounds 13 kg of *F. vulgare* fruit, purchased as a commercially available product, were dried for 3 days at 60 C.° in an oven. The sample was finely powdered using a blender, and it was then extracted twice with 100 L of methanol at room temperature for 2 days. The extract was filtered with Toyo filter paper No2 (Japan) and concentrated in vacuo at 35 C.° to obtain a 6% yield of methanol extract from the *F. vulgare* fruits, after filtering. The yield of methanol extract was calculated by weight of the ground *F. vulgare* fruits to that of methanol extract. 780 g of methanol extract were sequentially partitioned by polarity and density of organic solvents and then 20 g of methanol extract were partitioned into n-hexane (18.6 g), chloroform (0.8 g), ethyl acetate (0.1 g), and a water-soluble portion (0.5 g)

Test 1

Repellent activity of the methanol extract, hexane, chloroform, ethyl acetate and the water-soluble portion prepared by Example 1 was determined Test Insect

*Aedes aegypti* were used in the tests of mosquito repellency in the experiments of the present invention. They were provided from the National Institute of Health in Korea and were selected from indoor breeding insects that were not exposed to insecticides or other drugs. Larvae were reared in 30×35×10 cm cages. The first and second instar larvae sets were provided with fine filtered bovine feed and yeast in a ratio of 5 to 5, and third and fourth instar larvae sets were provided with coarse bovine feed and yeast in a ratio of 3 to 7. The pupae were transferred to a paper-cup using a spoide and then the paper-cup was moved to a cage being a structure (35×35×35 cm) made from wire. After the pupae emerged to adults in the cage, Adult mosquitoes were provided with cotton wool wetted with an 8% solution of sugared water for feed and were maintained at 27±3° C. and 80±10% RH (relative humidity) under a 16:8 (light:dark) hr light cycle.

Patch Test

To identify repelling effects on mosquitoes, there are methods using animals and methods using humans. The results of methods using animals may differ from those using humans. The methods using humans do not identify effects rapidly, because of complications in the experimental process and damage to human volunteer.

In the present invention, repellent activity was determined using an indoor experiment, a modified method of Schreck et al. (1977), that directly applies to humans and does not damage volunteer.

For patch test, 35×35×35 cm screen wire cage were used. Tests were conducted on nulliparous females 7–10 days old. The methanol extract and 4 types of portions prepared in the Example 1 and 100 µl of ethanol were applied to a piece of gauze (50 mm-diameter). After drying in the air for 2 minutes, the gauze was put on a rubber glove with a 50 mm-diameter hole punched in it and it was exposed in a cage (35×35×35 cm containing 60 mosquitoes). Because the gauze on the rubber glove was 5 mm away from the skin, mosquitoes would probe through the gauze in an attempt to feed but could not reach the back of the hand.

Repellent activity was measured by the number of mosquitoes landing on the gauze for 5 minutes. An untreated gauze (95% ethanol only) was also exposed to mosquitoes in the same manner and considered as a control. The degree of repellency was expressed in terms of percent repellency calculated according to the following equation.

$$\text{Repellency}(\%) = \frac{\text{No. landing mosquitoes in control} - \text{No. landing mosquitoes in treated}}{\text{No. landing mosquitoes in control}} \quad \text{[Equation 1]}$$

Also, in order to identify mosquito repelling activity, it was compared with synthetic repellent DEET by recording the number of landings.

Repellent activity of methanol extracts and the 4 portions of Example 1 against *A. aegypti* is shown in Table 1. The methanol extract and the hexane portion showed potent repellent activity against *A. aegypti*.

TABLE 1

| Sample | Dose (mg/cm$^2$) | Repellency (%) |
|---|---|---|
| Methanol extracts | 0.1 | > 80 % |
| Hexane portion | 0.1 | > 80 % |
| Chloroform portion | 0.1 | < 60 % |
| Ethanol portion | 0.1 | < 60 % |
| Water soluble portion | 0.1 | < 60 % |
| DEET | 0.1 | > 80 % |

EXAMPLE 2

The active compounds of the hexane portion (720 g) that present strong repellent activity were isolated.

FIG. 1 shows the procedure that isolates the active compound of the hexane portion.

The Primary Chromatography

The hexane portion (187 g) was chromatographed on a silica gel column (Berck 70–230 mesh, 600 g, 5.5 i.d.×70 cm), and successively eluted with a stepwise gradient of hexane-ethyl acetate. The ratios of hexane to ethyl acetate used in the stepwise gradient were 90:10, 85:15, 73:30, 50:50, and 0:100, and fractions of each ratio were collected as H1, H2, H3, H4 and H5 respectively. The five fractions were tested as to their mosquito repellency by the patch test of Test 1, and as a result, the two fractions, H1 (187 g) and H4 (57 g) that have repellent activity were isolated.

The Second Chromatography

The active fractions isolated from the first silica gel chromatography were chromatographed.

Firstly, the H1 fraction was eluted with hexane-ethyl acetate (20:1) and each eluent was named serially H11, H12 and H13. Also, to identify the active fraction, the three fractions H11, H12 and H13 were tested for mosquito repellency with the patch test, and as a result, the H11 fraction was found to be the active fraction.

On the other hand, the H4 fraction was also eluted with hexane-ethyl acetate (2:1) and each eluent was named serially H41, H42 and H43. Also, to identify the active fraction, the three fractions, H41, H42 and H43 were tested for mosquito repellency with the patch test, and as a result, the H41 fraction was found to be the active fraction.

The Third Chromatography

The active fractions H11 and H41 that were isolated from the second silica gel chromatography were further chromatographed.

The H11 fraction was eluted with hexane-ethyl acetate (30:1) in silica gel chromatography and then the active fraction H111 and the inert fraction H112 were isolated.

The H41 fraction was eluted with chloroform in silica gel chromatography and the active fraction H412 and the inert fractions H411 and H413 were isolated.

The Fourth Chromatography

The active fractions H111 and H412 that were isolated from the third silica gel chromatography were chromatographed.

The H111 fraction was eluted with hexane-ethyl acetate (35:1) in silica gel chromatography and then the active fraction H1111 and the inert fraction H1112 were isolated.

The H412 fraction was eluted with chloroform in semi-prep HPLC. The column was a 7.8 i.d.×300 mm (Phenomenex, $C_{18}$) and it was chromatographed in tetrahydrofuran-methanol-water (1:8:1) at a flow rate of 4.0 ml/min. Finally, 15 g of the potent active principles (compound II) were isolated.

The Fifth Chromatography

The active fraction H1111 isolated from the fourth chromatography was chromatographed.

The H1111 fraction was eluted with hexane-ethyl acetate (40:1) in silica gel chromatography and then the active fraction H11113 was isolated.

Also, the H11113 fraction was eluted in a μ porasil silica column. The column was 19 i.d.×300 mm (Waters, silica) and the fraction was chromatographed in hexane-ethyl acetate (98:2) at a flow rate of 4.0 ml/min. Finally, 4 g of the potent active principles (compound I) were isolated.

EXAMPLE 3

Identification of the Active Compounds

Structural determination of the active fractions isolated from Example 2 was made by spectral analysis. $^1$H- and $^{13}$C-NMR spectra were recorded with a JNM-LA 400F7 spectrometer (TMS as an internal standard), and chemical shifts were given in ppm. The electron impact (EI) UV spectra were obtained on a UV spectrometer (Kontron Instrument UVIKON 922) and mass spectra were obtained on a JEOL GSX 400 spectrometer. The two active compounds isolated from Example 2 were characterized as fenchone and E-9-octadecenoic acid as in the following Formulae 1 and 2.

[Formulae 1]

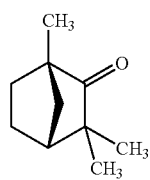

[Formulae 2]

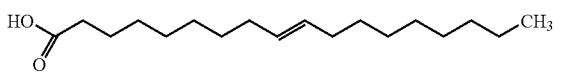

Test 2

Patch Test

The repellent activity of fenchone and E-9-octadecenoic acid against *A. aegypti* was determined by patch tests, and the results are shown in Table 2.

TABLE 2

| Dose | Repellency(average ± standard deviation, %)[a] | | |
|---|---|---|---|
| (mg/cm$^2$) | DEET | Fenchone | E-9-octadecenoic acid |
| 0.004 | 100a | 100a | 100a |
| 0.02 | 100a | 100a | 98.6 ± 0.9a |
| 0.01 | 96.4 ± 0.5b | 93.9 ± 0.6b | 91.1 ± 0.2b |
| 0.005 | 84.6 ± 1.3c | 82.1 ± 0.7c | 73.4 ± 2.3c |

Among a, b and c of the above Table 2[a], the same letter represents identification in the statistics (P=0.05, Scheffe's test). The repellency was transformed to arcsine square-root values.

In the patch tests at 0.01 mg/cm$^2$, the activity of both fenchone and E-9-octadecenoic acid showed potent repellency comparable with that of DEET. At 0.005 mg/cm$^2$, although repellent activity of both fenchone and E-9-octadecenoic acid was slightly lower than that of DEET activity (84.6%), both compounds (82.1% and 73.4%) were still very active.

Skin Test

In order to exactly confirm mosquito repellent activity, the compounds containing repellent activity were further examined by a skin test directly against skin. The cage was covered with a 35×35×35 cm mail net structure. Tests were conducted against nulliparous females 7–10 days old. Both compounds, in 100 μl of ethanol, were applied to a rubber glove surface with a 50 mm diameter hole punched on the hand. After drying in the air for 1 minute, skin was exposed for 5 minutes in a cage containing 60 mosquitoes. Repellent activity was measured by the number of mosquitoes biting the skin. The control treated only with 95% ethanol was also exposed to mosquitoes in the same manner.

The degree of repellency was expressed in terms of percent repellency calculated according to the following Equation 2.

$$\text{Repellency}(\%) = \frac{\text{No. biting mosquitoes in control} - \text{No. biting mosquitoes in treated}}{\text{No. biting mosquitoes in control}} \quad [\text{Equation 2}]$$

Also, repellent activity of DEET was examined in the same manner and the results are shown in Table 3.

TABLE 3

| Dose | Repellency(average ± standard deviation, %)a | | |
|---|---|---|---|
| (mg/cm$^{2)}$) | DEET | Fenchone | E-9-octadecenoic acid |
| 0.4 | 100a | 100a | 80.4 ± 0.2 |
| 0.2 | 100a | 100a | 52.3 ± 0.9 |
| 0.1 | 100a | 91.7 ± 0.9b | |
| 0.04 | 98.4 ± 0.5b | 76.2 ± 0.2c | |

A skin test treating skin directly was also performed, with a greater amount of the compound than with the patch test. At 0.4 mg/cm$^2$, fenchone had a perfect repellent activity, the same as DEET, and the E-9-octadecenoic acid had an 80.4% repellency.

As described above, repellent constituents isolated from *F. vulgare* fruits were identified as methanol extract, (+)-fenchone and E-9-octadecenoic acid. The fennel oil, (+)-fenchone and E-9-octadecenoic acid of the present invention can be provided as substitutes for the synthetic repellent DEET due to their lack of toxicity to people and their repellent activity against insects.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for repelling mosquito by using (+)-fenchone as an active ingredient in the amount effective to repel mosquito.

2. The method according to claim 1, wherein (+)-fenchone is isolated from a fennel oil, or a methanol extract or a hexane extract of *Foeniculum vulgare* fruit.

3. The method according to claim 1, wherein (+)-fenchone is used in combination with E-9-octadecenoic acid.

4. A mosquito repellent composition consisting of: as a sole active ingredient E-9-octadecenoic acid in an amount effective to repel mosquitoes from biting a human wherein E-9-octadecenoic acid is extracted from *Foeniculum vulgare* as a compound.

5. A mosquito repellent composition consisting of as a sole active ingredient E-9-octadecenoic acid being present from 30 wt % to 35 wt % of the composition, the composition being effective to repel a mosquito from biting a human.

* * * * *